United States Patent [19]
Volk

[11] Patent Number: 5,784,147
[45] Date of Patent: *Jul. 21, 1998

[54] INDIRECT OPHTHALMOSCOPY LENS SYSTEM

[76] Inventor: Donald A. Volk, 7893 Enterprise Dr., Mentor, Ohio 44060

[*] Notice: The term of this patent shall not extend beyond the expiration date of Pat. No. 5,479,222.

[21] Appl. No.: 580,872

[22] Filed: Dec. 22, 1995

Related U.S. Application Data

[63] Continuation of Ser. No. 152,189, Nov. 15, 1993, Pat. No. 5,479,222.

[51] Int. Cl.⁶ ............................................. A61B 3/00
[52] U.S. Cl. ................................. 351/219; 351/205
[58] Field of Search ........................... 351/219, 160 R, 351/205, 247, 246

[56] References Cited

U.S. PATENT DOCUMENTS

| | | |
|---|---|---|
| 4,307,944 | 12/1981 | Schirmer. |
| 4,469,413 | 9/1984 | Shirayanagi. |
| 4,627,694 | 12/1986 | Volk. |
| 4,682,866 | 7/1987 | Volk. |
| 4,721,378 | 1/1988 | Volk ........................................ 351/205 |
| 4,728,183 | 3/1988 | Heacock. |
| 4,738,521 | 4/1988 | Volk. |
| 5,007,729 | 4/1991 | Erickson et al.. |
| 5,046,836 | 9/1991 | Volk ........................................ 351/219 |
| 5,309,187 | 5/1994 | Crossman et al.. |
| 5,479,222 | 12/1995 | Volk ........................................ 351/219 |

OTHER PUBLICATIONS

"Conoid Lenses for Indirect Ophthalmoscopy" by David Volk, MD, International Ophthalmology Clinics, Refraction—Aspheric Opthalmic Lenses, Jun., 1965, vol. 5, No. 2.

*Primary Examiner*—Hung X. Dang
*Attorney, Agent, or Firm*—Oldham & Oldham Co., L.P.A.

[57] ABSTRACT

The invention is directed to an ophthalmoscopic or gonioscopic lens system as well as an adapter lens systems for use with such an associated lens apparatus. The indirect ophthalmoscopy lens of the invention for use in examination or laser treatment of a patient's eye comprises a hand-held, pre-set or fixed system having at least two lens elements, each having first and second surfaces. At least one of the lens elements includes an aspheric surface of revolution. The at least two lens elements are positioned adjacent one another in a housing, such that the refractive properties of each are combined to converge light from an illumination light source to the entrance pupil of the patient's eye to illuminate the fundus thereof and form a fundus image to be viewed. The adapter lens systems of this invention are designed for use with an associated ophthalmoscopic lens, enabling selective modification of the optical characteristics of the ophthalmoscopic lens system in a predetermined manner. Within the scope of this invention, a plurality of attachments make possible change in the net power, optical imaging characteristics, magnification, laser transmission properties or other characteristics of a particular ophthalmoscopic lens.

31 Claims, 4 Drawing Sheets

INDIRECT OPHTHALMOSCOPY LENS SYSTEM

This is a continuation of application Ser. No. 08/152,189 now U.S. Pat. No. 5,479,222 filed on Nov. 15, 1993.

TECHNICAL FIELD

The invention relates generally to lens systems and adapter lens systems for use in ophthalmic examination or treatment procedures. More particularly, the invention relates to improved direct and indirect ophthalmoscopy lens systems and associated adapter lenses designed for use with standard ophthalmic instruments providing specific and desired magnification and imaging characteristics for improved examination or treatment of the eye.

BACKGROUND OF THE INVENTION

Indirect ophthalmoscopy techniques are used in diagnostic, therapeutic and surgical procedures in the field of ophthalmology, and normally include the use of positive power lens systems in conjunction with an observing optical system such as a indirect ophthalmoscope, slit lamp biomicroscope, or operating microscope. Lenses conventionally used in indirect ophthalmoscopy applications often perform the dual functions of condensing light from a light source toward the pupil of the eye to illuminate the fundus, and forming an inverted real aerial image of the fundus which can be viewed with either a monocular or binocular device. Indirect ophthalmoscopy systems have been found to be superior to other examination or treatment methods, in particular in the examination of a retinopathies, retinal separation, retinal tumors, intraocular foreign bodies, and provide the ability to see fundus lesions which otherwise may not be observable when opacities of the ocular media are present. Hand-held lenses used in indirect ophthalmoscopy have been of a variety of types, each affording various advantages in the examination of the fundus. In the development of indirect ophthalmoscopy, hand-held lenses originally comprised a single lens element having plano and/or convex spherical surfaces and were of low power. The aerial image produced with such a lens was magnified and inverted, and considerably blurred, particularly toward the periphery of the formed aerial image. A two-element Ramsden style indirect ophthalmoscopy lens was thereafter produced by Rodenstock utilizing a spherical convex surface on each of the lens elements. This lens provided improved optical quality over that of a single lens using spherical surfaces, but resulted in increased surface reflections and light loss which outweighed the limited benefits of the insufficiently improved image quality. There has also been reported the use of a "periscopic lens" for use in slit lamp funduscopy. The periscopic lens included a double plano-convex lens system similar to the Ramsden style indirect ophthalmoscopy lens, but of smaller diameter and higher power. The periscopic lens system also utilized spherical surfaces, such that only limited improvement in optical quality was realized and a reduced field of view was obtained.

Subsequently, improvements were noted by the use of slightly higher powered single element lenses, each having one aspheric surface with the other surface being plano or spherical. Although the use of a single aspherical surface in the indirect ophthalmoscopy lens did show great improvement over spherical indirect ophthalmoscopy lenses, lens aberrations remained. Thus, the formed aerial image of the fundus still had aberrations and increasing astigmatic effects particularly in the peripheral regions of the image.

These designs were subsequently improved upon by the use of two aspherical surfaces incorporated into the indirect ophthalmoscopy lens. The first use of a double aspheric indirect ophthalmoscopy lens designed for use with an indirect ophthalmoscope was described in U.S. Pat. No. 4,738,521 by David Volk. This lens design incorporates both front and back aspheric surfaces of revolution of conoid type, which substantially improved the quality of the formed aerial image by reducing aberrations including field curvature, astigmatism and distortion. The use of double aspheric lenses has been found to be a distinct advantage in indirect ophthalmoscopy and has made possible the use of much stronger lenses while providing increased clarity of the image as well as increased field of view. More recently, a symmetrical double aspherical indirect ophthalmoscopy lens particularly suited for use with a slit lamp biomicroscope was developed by David Volk, and described in U.S. Pat. No. 4,627,694. The double aspheric lenses shown in this patent were of smaller diameter and higher power, with the aspheric surfaces described as providing improved correction of aberrations, including field curvature, astigmatism, and distortion. Lenses made according to this design have demonstrated themselves to be better suited for use with the slit lamp biomicroscope, and have yielded significant improvement in the examiner's ability to see details in the aerial image of the fundus. The single element double aspheric lens thus provided improved imaging as well as wide field viewing of the fundus, particularly for use with a slit lamp biomicroscope.

In the development of indirect ophthalmoscopy lens systems, it is seen that particular lenses are best for use with a slit lamp or other biomicroscope, while other lens systems are more suited for use with an indirect ophthalmoscope or other observation system. For example, the longer focal length, lower power indirect ophthalmoscopy lens systems are not suitable for use with a slit lamp biomicroscope, as the observation of the formed aerial image would require positioning of the biomicroscope at a location which exceeds the range of travel built into the instrument. The development of the double aspheric indirect ophthalmoscopy lens as described above has enabled use of higher power lenses to provide a shorter working distance within the range of adjustment of the slit lamp biomicroscope to facilitate its use as the observation optical system, instead of an indirect ophthalmoscope or the like. It thus may be seen that a particular diagnostic or therapeutic procedure may require the use of a lens system which is particularly designed for that procedure only, thus requiring the practitioner to purchase and maintain a variety of lens systems on hand to achieve the best results for other particular procedures. Based upon the foregoing, it is clearly desirable to provide the practitioner an indirect ophthalmoscopy lens system which may be modified in a specific and pre-determined manner, such that a variety of examination or treatment procedures are possible.

Similar in this respect to indirect ophthalmoscopy lens systems, other ophthalmic lens systems have inherent limitations as it relates to examination or treatment procedures. For example, direct ophthalmoscopic observation techniques utilize a direct ophthalmoscopy lens system which produce a virtual image of the eye fundus having particular magnification characteristics. With both such direct and indirect ophthalmoscopic lens systems, there exists no ability to modify the inherent magnification, field, or imaging characteristics of the system, thereby limiting their use. Similarly, gonioscopic lenses for examination and treatment of the anterior chamber angle of the eye are also limited in optical performance, having specific magnification and field characteristics. In these various lens systems for examination and treatment of the eye, no provision exists for the modification of inherent imaging characteristics of the lens itself and thus the resulting field characteristics and magnification of the produced virtual or aerial image. Only with the slit lamp biomicroscope or operating microscope does there exist the ability to change magnification, not of the viewed image itself, but as a secondary adjustment of the Keplerian telescope observation system.

SUMMARY OF THE INVENTION

Based upon the foregoing, it is a main object of the present invention to provide an ophthalmoscopic lens system which enables its imaging and/or magnification characteristics to be modified in a predetermined manner to facilitate its use in a particular diagnostic or treatment procedure.

Another object of the invention is to provide an indirect ophthalmoscopy lens system which utilizes at least two lens elements cooperating with one another to enhance light condensing functions of the lens system for illumination of the eye fundus, as well as imaging characteristics of the lens.

A further object of the invention is to provide adapter lens systems for use with an associated ophthalmoscopic or gonioscopic lens system to allow the characteristics of the ophthalmoscopic or gonioscopic lens system to be modified in a predetermined manner.

The invention is therefore directed to an ophthalmoscopic or gonioscopic lens system as well as an adapter lens systems for use with such an associated lens apparatus. The indirect ophthalmoscopy lens of the invention for use in examination or laser treatment of a patient's eye comprises a hand-held, pre-set or fixed system having at least two lens elements, each having first and second surfaces. At least one of the lens elements includes an aspheric surface of revolution with its magnitude and shape defined by the polynomial expressed as follows:

$$y=(2rx+(e^2-1)x^2)^{1/2}+Ax^F+Bx^G+Cx^H;$$

where r equals the apical radius of curvature of each surface, e equals the apical eccentricity of each surface, and coefficients A, B, and C, when used, represent successive terms in the polynomial, and F, G, and H equal exponents in the successive terms. The at least one aspheric surface of the lens system is chosen to correct astigmatic imagery of the lens, such that the lens system forms an aerial image substantially free of excessive field curvature and astigmatism. The indirect ophthalmoscopy lens system may be adapted to be hand held, with the at least two lens elements being positioned adjacent one another in a housing, such that the refractive properties of each are combined to converge light from an illumination light source to the entrance pupil of the patient's eye to illuminate the fundus thereof The at least two lens elements are held relative to the patient's eye at a distance corresponding to the secondary focal distance of the lens elements with their refractive properties combined.

The adapter lens systems of this invention are designed for use with an associated ophthalmoscopic lens, enabling selective modification of the optical characteristics of the ophthalmoscopic lens system in a predetermined manner. Within the scope of this invention, a plurality of attachments make possible change in the net power, optical imaging characteristics, magnification, laser transmission properties or other characteristics of a particular ophthalmoscopic lens.

The adapter lens system comprises at least one adapter lens element including first and second surfaces positioned within an adapter housing. The adapter housing includes means for selective attachment to the housing associated with an ophthalmoscopic lens system, wherein upon attachment of the adapter housing to the housing of the ophthalmoscopic lens, the at least one adapter lens element is positioned in predetermined relationship to a lens of the ophthalmoscopic lens device so as to modify the optical characteristics of the ophthalmoscopic lens system in a selective and predetermined manner.

BRIEF DESCRIPTION OF THE DRAWINGS

A better understanding of the invention will be obtained upon a further reading of the detailed description in conjunction with the drawings wherein.

DETAILED DESCRIPTION OF THE INVENTION

Figure 1:
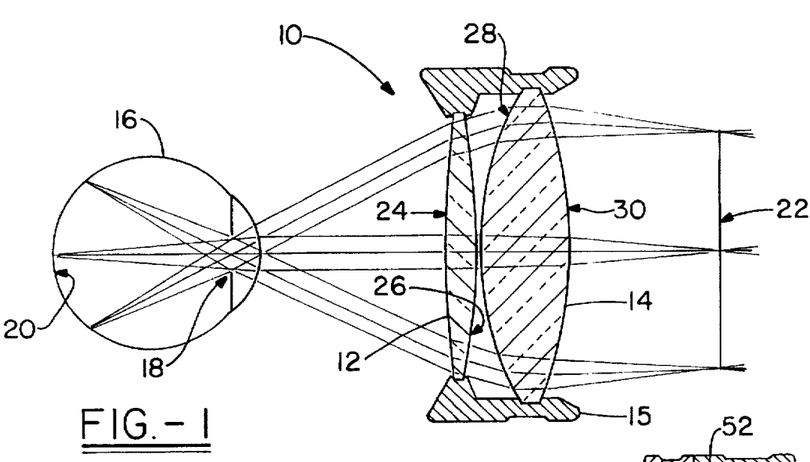
FIG. 1 is a schematic illustration of an indirect ophthalmoscopy lens system in accordance with the invention.

An indirect ophthalmoscopic lens system in accordance with a first aspect of the invention is shown in FIG. 1, wherein the lens system 10 includes at least two lens elements, with a first lens 12 positioned relative to a second lens 14 in a housing 15. The lenses 12 and 14 condense light from an illumination light source into a patient's eye 16 through pupil 18 and onto fundus 20 thereof. In order to obtain the widest illumination of the fundus 20, the lens system 10 is positioned at a distance from the patient's eye 16, and particularly the pupil 18 thereof, such that the back focus of the combined lenses 12 and 14 substantially coincides with the pupil 18. The lens system 10 also gathers light rays emerging from points on the fundus 20 at an image plane 22. The fundus image is a sharp, clear, aberration-free aerial image which can be viewed using an indirect ophthalmoscope or slit lamp biomicroscope for example. The fundus image is formed as an aerial image posterior to the indirect ophthalmoscopy lens system 10. Assuming that the eye 16 is an emmetropic eye, each bundle of light rays emerging from the eye will be a substantially parallel bundle, with its chief ray passing through the center of the pupil 18. These light rays will be incident upon the indirect ophthalmoscopy lens system 10, initially refracted by the first surface 24 and second surface 26 of lens 12. The light rays are thereafter incident upon lens 14, and further refracted by lens surfaces 28 and 30 and focused at the image plane 22. The bundles of light rays converged by indirect ophthalmoscopy lens system 10 will be focused to single points on the image plane 22, with points on the fundus 20 of eye 16 being represented in the formed aerial image.

The lenses 12 and 14 may be made of a homogenous transparent optical material, such as ophthalmic grade glass or plastic. In a preferred embodiment, both lens 12 and lens 14 are made of high-grade optical glass having an index of refraction between 1.4 and 1.9, and preferably with an index of refraction of 1.883 as an example, for at least one of the lens elements. Manufacture of the lens 12 is simplified by utilizing spherical surfaces 24 and 26. In the preferred embodiment, the spherical surfaces 24 and 26 are related in a ratio of approximately 1:3, with the steeper curve of surface 26 facing second lens 14. Similarly, a steeper curve is provided on surface 28 of lens 14 facing lens 12. In the preferred embodiment, surface 28 will be an aspherical surface of revolution, having its magnitude and shape described by the polynomial expressed as follows:

$$y=(2rx+(e^2-1)x^2)^{1/2}+Ax^F+Bx^G+Cx^H;$$

where r equals the apical radius of curvature of the surface, e equals apical eccentricity of the surface, and the co-efficients A, B, and C, when used, equal successive terms in the polynomial, with F, G, and H equaling exponents in the successive terms. The aspherical surface 28 will be relatively steeply curved in relation to surface 30 of lens 14, such that the more highly curved surfaces of each of the lens 12 and 14 face one another. It has been found that by facing the more steeply curved surfaces of the lenses toward one another, spherical aberration induced from the spherical surfaces in the lens system can be minimized to a great degree. Additionally, the aspherical surface 28 provides required additional correction of spherical aberration as well as primary field correction to produce a sharp, clear fundus image. In a preferred embodiment, surface 30 of the lens 14 is formed as a spherical surface, again being more easily and cost effectively produced as compared to an aspherical surface on such a lens. Planar surfaces may also be used if desired. The provision of at least one aspherical surface of revolution in the indirect ophthalmoscopy lens system 10 allows for correction of primary field aberrations in association with the self-correcting relationship of the lenses 12 and 14, while allowing cost-effective production of the lens system using additional spherical surfaces. In the indirect ophthalmoscopy lens system, the nominal powers of each of the lens 12 and 14 are chosen to yield a nominal power for the indirect ophthalmoscopy lens system 10 of a desired magnitude. Generally, the indirect ophthalmoscopy lens system 10 of the invention may be designed having a nominal power in range between 10 to 150 diopters, with lower power lens systems being useful in indirect ophthalmoscopy techniques where high magnification of the fundus image is desired. Higher magnification allows much more detail of the fundus pathology to be viewed for examination or treatment.

Alternatively, high power lens systems 10, which are particularly useful with the slit lamp biomicroscope, may be used to provide a wide field view of the fundus. The use of at least two lenses allows significant latitude in the particular design criteria for each of the lenses 12 and 14, while optimizing the light condensing and imaging-forming qualities of the lens system.

It is also a feature of the invention to provide a system by which an ophthalmic lens system can be modified for various diagnostic or treatment uses in a simple and effective manner. For example, given an indirect ophthalmoscopy lens having a nominal power to achieve predetermined magnification, field size and imaging characteristics, the present invention enables adaptation of an additional lens or lenses, of either positive or negative power, to the ophthalmoscopy lens, thus providing altered magnification, field size and/or field imaging characteristics for various examination or treatment requirements.

Figure 2:
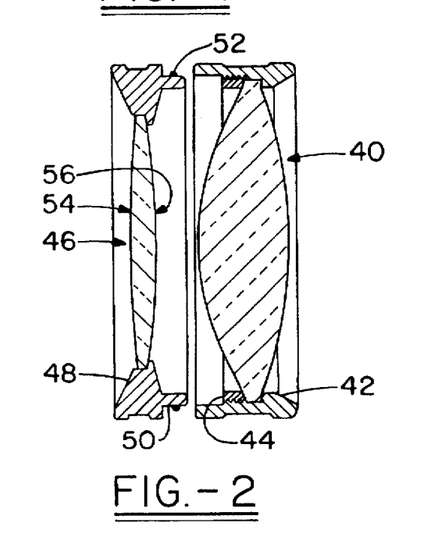
FIG. 2 shows a first embodiment of an adapter lens system in accordance with the invention.

In FIG. 2, a first example of an adapter lens system is shown for use with a commercially available indirect ophthalmoscopy lens. As an example, an indirect ophthalmoscopy lens 40 may be the commercially available Volk Double Aspheric 20D lens produced by Volk Optical, Inc. Such a lens is described in U.S. Pat. No. 4,738,521 issued to David Volk. In general, a 20 diopter lens of this type will form an aerial image of the fundus of the eye viewed monocularly using a monocular indirect ophthalmoscope, or binocularly and stereoscopically with a binocular indirect ophthalmoscope at approximately 3× magnification. Although the 20 diopter indirect ophthalmoscopy lens 40 provides magnification characteristics which are best suited for observing fine details of the fundus, if additional examination or treatment procedures are desired to be performed, another indirect ophthalmoscopy lens of a different power may be more suited to the task. In accordance with this invention, modification of the indirect ophthalmoscopy lens 40 may be made to allow other beneficial uses in examination or treatment of the patient's eye. Referring to FIG. 2, lens 40 is positioned within a conventional retainer housing 42, and may be fixed in position by means of a lens retaining ring 44 screwed into place after insertion of lens 40 into housing 42. The adapter lens system of the invention comprises one or more additional lenses 46 mounted in an adapter housing 48. The adapter housing 48 may be selectively attached to the housing 42 of the indirect ophthalmoscopy lens 40 on either side of the lens 40 for use in conjunction therewith. For attachment to the indirect ophthalmoscopy lens housing 42, the adapter lens housing 48 may include an engageable flexible section 50 having an outer diameter slightly larger than the inner diameter of the housing 42. Alternatively, a compressible and resilient o-ring 52 may be used to frictionally engage the inner surface of housing 42, or other suitable means such as resilient fingers may be used to frictionally engage housing 42. Screw threads or any other suitable means may also be used for selective attachment of the adapter lens housing 48 to the indirect ophthahnoscopy lens housing 42. The use of an o-ring 52 allows an air and watertight seal to be formed, protecting the interior lens surfaces from water or contamination. The o-ring 52 may be integrally formed in the adapter housing section 50 or may be provided as a separate member set in a groove machined around the circumference of area 50 as desired. The resilient engaging means of the adapter lens housing 48 allows selective engagement with a wide variety of commercial indirect ophthalmoscopy lens housings as desired. The adapter lens housing 48 may be easily grasped around an external knurled circumference for example, for engagement with or disengagement from indirect ophthalmoscopy lens housing 42.

Referring again to FIG. 2, adapter lens 46 comprises a first surface 54 and a second surface 56. The surfaces 54 and 56 are preferably spherical surfaces which are easily and cost effectively manufactured. In a desired configuration, the spherical surface 56 will have a radius of curvature in a ratio of approximately 3:1 to the curvature of surface 54, such that the more steeply curved surface 56 is positioned adjacent to indirect ophthalmoscopy lens 40. The adapter lens 46 may have a nominal power of 20 diopters, such that in association with the 20 diopter indirect ophthalmoscopy lens 40, a high net power combination system is created. With particular diagnostic and treatment applications in mind, a set of adapter lenses of varying powers may be provided.

As an example, a set of adapter lenses for use with 20 diopter double aspheric indirect ophthalmoscopy lens 40, such as shown in FIG. 2, may include lenses of approximately +4 diopters, +7 diopters, and +20 diopters (as shown in FIG. 2), for increasing the power of indirect ophthalmoscopy lens system 40. The adapter set may also include minus powered lenses. As an example, a lens of approximately −4 diopters may be utilized to reduce power and increase magnification. The adapter lenses may be cost effectively produced from a plastic material using aspheric surfaces, but other materials or surface configurations such as planar or spherical may also be used if desired.

Figure 2A:
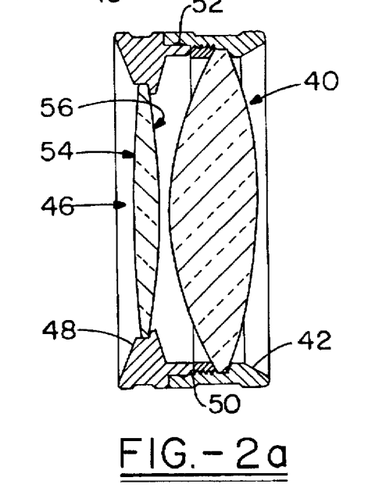
FIG. 2a shows the adapter lens system of FIG. 2 in use with an indirect ophthalmoscopy lens system.

According to the example above, FIG. 2a shows a preferred embodiment of the "+4D" adapter lens incorporates a symmetrical biconvex lens design with both radii 54 and 56 equal to 258 mm, a glass index is 1.519, a diameter of 50 mm, and a center thickness of 3.73 mm. The preferred "+7D" lens design may also be biconvex with both radii 54 and 56 equal to 155 mm, a glass index of 1.519, diameter of 50 mm, and center thickness of 5.28 mm. A preferred "−4D" lens design is meniscus in shape, having a concave radius 54 of 83 mm, a convex radius 56 of 235 mm, glass index is 1.519, diameter of 50 mm and center thickness of 1.25 mm. The convex surface may be positioned adjacent to the more highly curved surface of the 20D lens, with the concave surface facing the practitioner.

Figure 3:
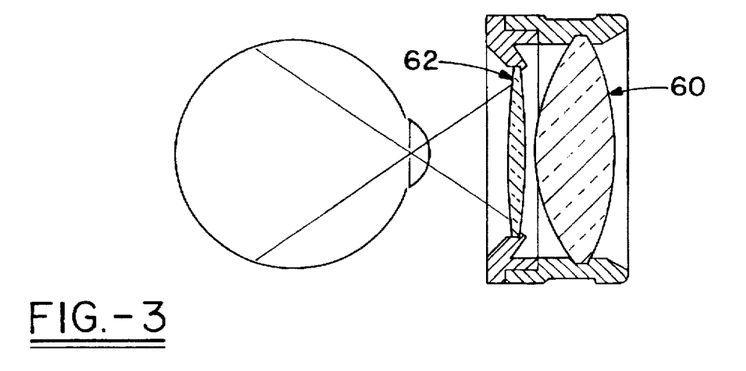
FIG. 3 shows an alternate embodiment of an adapter lens in use with an indirect ophthalmoscopy lens system.

In FIG. 3, a further embodiment of an adapter lens system is shown, designed for use with a commercially available 40 diopter indirect ophthalmoscopy lens, such as a double aspheric lens, 60, produced by Volk Optical, Inc. Similar to the previous example of FIG. 2, an adapter lens system comprising adapter lens 62 may be used in association with the indirect ophthalmoscopy lens 60 to selectively modify the magnification, field of view or imaging characteristics of the indirect ophthalmoscopy lens 60. In practice, the 40 diopter double aspheric indirect ophthalmoscopy lens 60 has a working distance as well as magnification and field size characteristics that make it useful with an indirect ophthalmoscope. The indirect ophthalmoscopy lens 60 is generally not suitable for use with a slit lamp biomicroscope, as the aerial fundus image is formed at a distance from the patient's eye which does not allow its observation, due to the limitations of the biomicroscope itself. Generally, the observation system of the slit lamp biomicroscope is movable between extreme positions to adjust to the position of the fundus image, but such adjustment is limited. Alone, the use of the 40 diopter indirect ophthalmoscopy lens would require positioning of the biomicroscope outside the range of its travel. The 40 diopter indirect ophthalmoscopy lens 60 may be combined with an adapter lens 62 also having a nominal power of 40 diopters. The resulting increased system power of combined lenses 60 and 62 provides an aerial fundus image viewable within the travel allowed by the slit lamp biomicroscope observation system. The addition of the adapter lens 62 to the optical system also significantly increases the field of view to allow the peripheral retina in the region of the equator and beyond to be viewed. The resulting lens system including adapter lens 62 may also be advantageously used for laser treatment of the eye fundus. In the embodiment of FIG. 3, other adapter lenses may be provided for use with indirect ophthalmoscopy lens 60 to achieve other characteristics if desired. The adapter lens 62 may also have spherical surfaces with the more steeply curved surface facing the indirect ophthalmoscopy lens 60 in the preferred embodiment. Alternatively, planar or aspherical surfaces may be used in the adapter lens system if desired.

Figure 4:
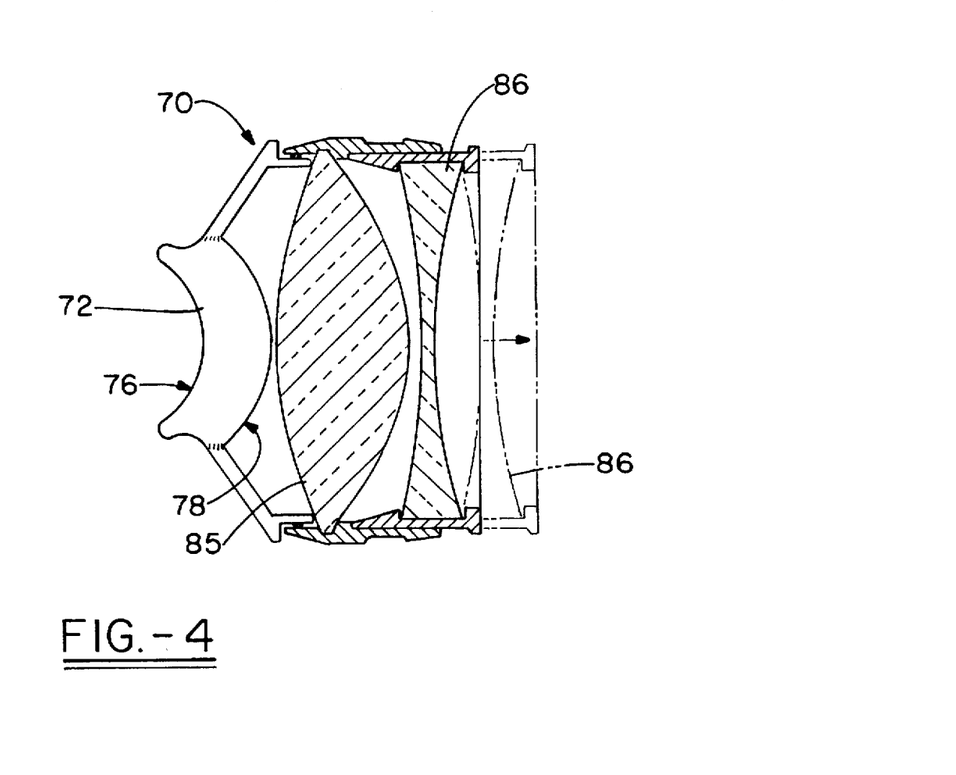
FIG. 4 shows a further embodiment of an adapter lens in use with an indirect ophthalmoscopy lens system.

In a further embodiment of an adapter lens system according the present invention, the adapter lens may be a contact lens or lens system used in conjunction with an indirect ophthalmoscopy lens to produce desired magnification, field of view, and imaging characteristics. Referring to FIG. 4, contact adapter lens 70 may be used in association with a hand-held indirect ophthalmoscopy lens 85, which in this example is a commercially available double aspheric lens produced by Volk Optical, Inc. Lens 85 represents a high powered lens designed for use with a slit lamp biomicroscope, having a nominal power, for example, in the range of 60 to 130 diopters, as described in U.S. Pat. No. 4,627,694, issued to David Volk. Lens 85, when used by itself produces a high resolution, wide field image of the fundus. The contact adapter lens 70 can be designed to selectively vary the power of the resulting indirect ophthalmoscopy lens 85, while providing the various mechanical advantages of using a contact lens device. The use of the contact lens 76 may facilitate proper positioning of the lens system components in relation to a patient's eye, and particularly the patient's pupil such that the conjugate focus of the slit lamp light source will be located at or near the center of the patient's pupil for wide field illumination of the fundus. The contact lens 76 may be of either positive or negative power, changing the focal length of the combined optical system and therefore the system's net power, with a variety of contact adapter lens powers enabling the desired net power and magnification of the combination lens system to be achieved.

Referring to FIG. 4, a preferred positive power contact design of contact lens 76 includes a corneal contacting surface 76 and an anterior surface 78, both of which may be spherical or aspherical in surface configuration. In the preferred embodiment, the corneal surface 76 has an apical radius of 7.65 mm and an eccentricity of 0.425, closely matching the aspherical corneal surface. Anterior surface 78 may have an apical radius of 6.29 mm and an eccentricity of 0.6, correcting for the spherical aberration of the high power contact lens. Center thickness of the contact lens may be selected as desired with a preferred thickness of 3 mm. Alternatively, the contact lens may be a negative power lens, with a preferred negative power contact design including a corneal contacting surface 76 and an anterior surface 78, again, both of which may be spherical or aspherical in surface configuration. In the preferred embodiment, the corneal surface 76 has an apical radius of 7.65 mm and an eccentricity of 0.425. Anterior surface may have an apical radius of 12.93 and be modelled as an oblate spheroid or ellipsoid with a (negative) eccentricity value of 0.7. Again, center thickness of the contact lens may be selected as desired, with a preferred center thickness of 1.35 mm. Also in FIG. 4, there is shown the possible use of a minus powered adapter lens 86 which is positioned on the anterior side of the indirect ophthalmoscopy lens 85. The minus powered lens 86 may also be supported within an adapter housing 88 which provides selective attachment of the adapter lens system to the indirect ophthalmoscopy lens housing. The minus power adapter lens 86 may include planar and/or spherical or aspherical surfaces as desired. The addition of a minus power lens 86 to the optical system will produce increased magnification and may be used either alone or in combination with a contact adapter lens or other adapter lens system positioned on the posterior side of the indirect ophthalmoscopy lens 85. Similarly, the minus powered lens 86 may be independently positioned on either side of the indirect ophthalmoscopy lens depending upon the particular characteristics desired.

It is also an aspect of the invention to provide an adapter lens housing which allows manual adjustment of the position of the adapter lens optical system relative to the indirect ophthalmoscopy lens system with which it is used. As an example, the adapter lens housing 88 for the minus powered lens 86 is selectively repositionable as shown in ghost to provide adjustment of the distance between the lenses 85 and 86. The adjustable positioning of lens 86 allows variable system power to be achieved using the same adapter lens. It should be recognized that upon positioning of the minus powered lens 86 in close proximity to indirect ophthalmoscopy lens 85, the system power will be reduced to the maximum degree. Upon moving lens 86 away from lens 85 as shown in ghost, the net power of the system will increase. Means may be provided in association with the adapter lens housing 88 to allow a plurality of specific positions relative to the indirect ophthalmoscopy lens 85 to be readily obtained, such as stops or detents which will precisely position the adapter lens system, such as lens 86 accordingly. For example, the adapter lens may be moved to provide 5 diopter incremental changes in system power or the like. This will allow net system power to be adjusted as desired for a particular clinical application. The other examples of adapter lenses shown herein may also be provided with housings to allow selective and variable positioning of the adapter lens system relative to the indirect ophthalmoscopy system.

Figure 5:
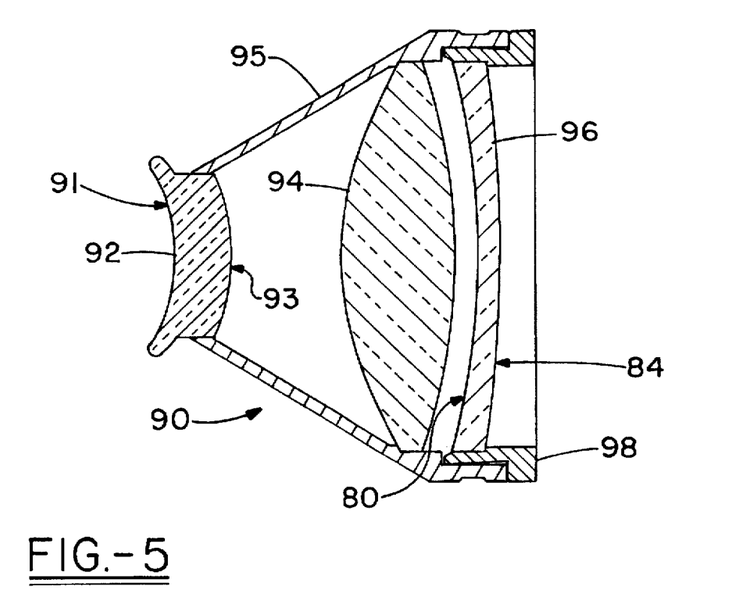
FIG. 5 shows an adapter lens system for use in association with a contact indirect ophthalmoscopy lens system.

Turning to FIG. 5, an embodiment of the adapter lens system according to the invention is shown in use with an indirect ophthalmoscopy lens system 90 which includes a contact lens 92 and an anterior image forming lens element 94. The indirect ophthalmoscopy lens system 90 may be similar to that described in U.S. Pat. No. 5,046,836 issued to Donald Volk, with various lenses as described by this patent being commercially available from Volk Optical, Inc. In use with such an indirect ophthalmoscopy lens, the adapter lenses of the invention may again used to vary the system power or imaging characteristics when combined with the contact indirect ophthalmoscopy lens system 90. As an example of the indirect ophthalmoscopy lens 90, the contact lens 92 may include an aspherical concave surface 91 which closely matches the contour of the cornea of the eye, and an aspherical anterior convex surface 93 if desired. The anterior lens element 94 may also be a single or double aspheric bi-convex lens, which in combination with the contact lens 92, forms a high resolution, wide-field fundus image having predetermined magnification and imaging characteristics. In one example, the magnification of the indirect ophthalmoscopy lens system 90 is 1.0 with a predetermined field of view of approximately 80°. It may be desirable to increase the magnification of the indirect ophthalmoscopy lens system 90 by addition of a negative power adapter lens, or alternatively to increase the field of view of the system using a positive power adapter lens. Examples of adapter lenses include both plus and minus powered lenses having from approximately −20 to +20 diopters. The adapter lens 96 and its associated housing 98 are selectively attached to the indirect ophthalmoscopy lens housing 95 in a manner similar to that previously described. The minus powered adapter lenses may be used to increase the magnification of the indirect ophthalmoscopy lens system 90 for diagnostic or laser treatment applications. As an example, an adapter lens having a nominal power of −14 diopters increases the magnification of the indirect ophthalmoscopy lens 90 to 1.4, in turn reducing the laser spot size an amount equal to the reciprocal of the lateral magnification of the lens for improved focal laser treatment in the central retinal area. In a preferred embodiment, the adapter lens 96 may be meniscus in shape with its concave surface 80 adjacent to the anterior surface of the contact indirect ophthalmoscopy glass imaging lens. The adapter lens concave surface 80 may be spherical with a radius of 17 mm and the convex side 84 may be an oblate spheroid with an apical radius of 31.2 mm and a (negative) eccentricity of 0.9. The diameter may be 26 mm, with a center thickness 1.25 mm, utilizing a glass with an index of refraction of 1.523. Although the addition of the adapter lens 96 to the indirect ophthalmoscopy lens system will result in a change of the focal length of the lens system and therefore also a change of its focus relative to the entrance pupil of a patient's eye, the benefits obtained by the addition of the adapter lens system outweigh a slight reduction in field size which may occur as a result of increased focal length. Alternatively, a positive power adapter lens 96 will increase the power of the optical system, decrease the fundus image magnification, increase field of view and further allow the slit lamp illumination to be angled further off-axis, so as to reduce reflections in the optical system.

Figure 6:
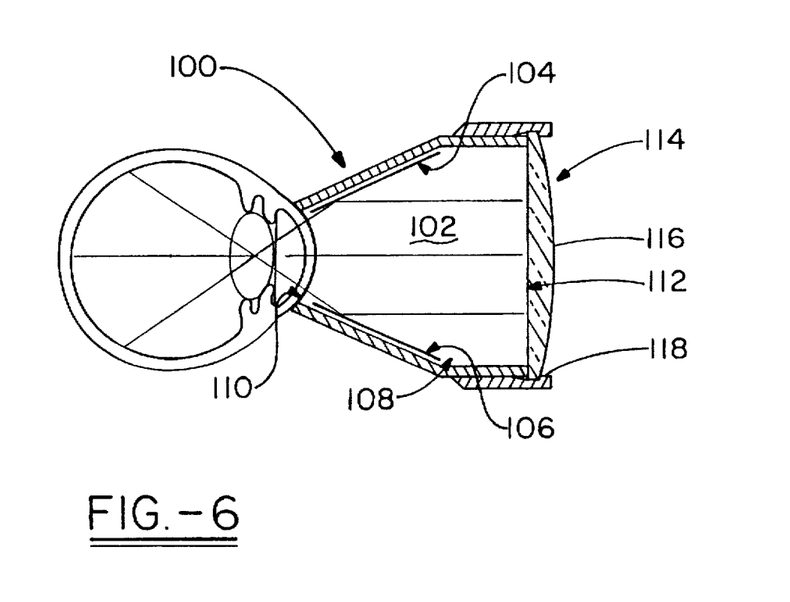
FIG. 6 shows an adapter lens system for use in association with a three-mirror ophthalmoscopic gonioscopic lens used for performing various diagnostic or treatment procedures.
Figure 6A:
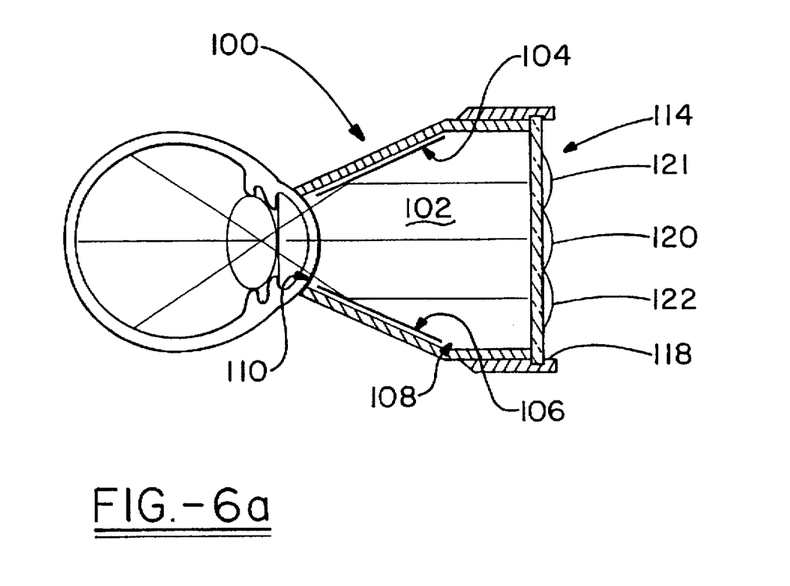
FIG. 6a shows an alternative embodiment of the adapter lens system as shown in FIG. 6.

The adapter lens systems of the present invention may also be useful with other types of ophthalmoscopic optical devices, such as direct ophthalmoscopy lenses or gonioscopy lenses, and the like. In FIG. 6, a known Goldmann type three-mirror lens 100 is shown, which performs several useful diagnostic functions. In such a lens, a series of reflecting surfaces 102, 104, and 106 are provided within a contact lens 108. The contact lens 108 has a contact surface 110 and an anterior planar surface 112. Surfaces 102, 104, and 106 are inclined at varying angles to the anterior surface 112. The semi-circular mirror 102 is used for gonioscopy, while rectangular mirrors 104 and 106 are used for examination of the retrociliary region as well as peripheral regions of the retina. The posterior pole may also be observable through the axis of the contact lens 108. In use with such a lens, an adapter lens system 114 of the invention may vary the magnification, field size, or imaging characteristics of the lens in a variety of manners. For gonioscopy, a lower magnification may be preferred for studying the contours of the anterior chamber angle, wherein a minus power lens (not shown) may be effectively used for such a purpose. Alternatively, to better view the trabecular meshwork of the anterior chamber angle, higher magnification may be desirable, provided by means of a plus power adapter lens 116 or series of small adapter lenses 120, 121, and 122 as shown in FIG. 6a, each of which are disposed in a housing 118. In FIG. 6a, the small adapter lenses 120–122 are provided for each of the mirrors 102, 104, and 106 respectively, as well as for the central fundus view. The adapter lenses 120–122 allow observation of the images from each of the mirrors through central portion of each lens 120–122. Surfaces of such an adapter lens may appropriately be plano, concave, or convex and may be aspherical in contour to enhance imaging properties. Thus the virtual image produced by such gonioscopy and direct ophthalmoscopy lenses may be magnified without distortion.

Figure 7:
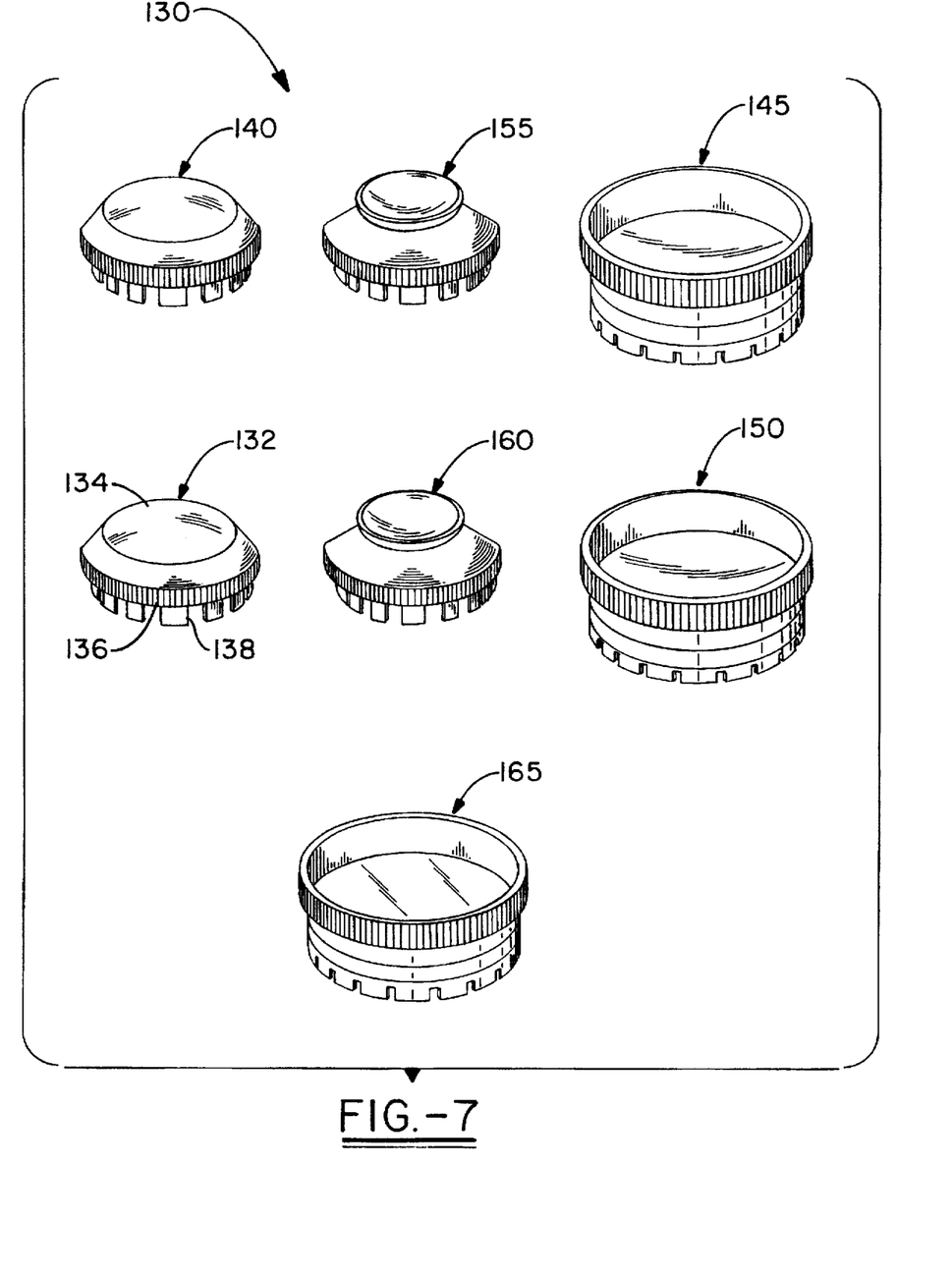
FIG. 7 shows a set of adapter lenses in accordance with the invention.

In FIG. 7, a set of adapter lens systems according to the invention are shown, with the set generally designated 130 comprising at least two adapter lens systems, each having at least one adapter lens element. In the adapter lens set 130, the adapter lens systems may include positive and negative power lens systems, and may also include contact and non-contact lens systems. More particularly, as shown in FIG. 7, the set 130 may include a plus powered adapter lens system 132 having a plus powered lens element 134 positioned within an adapter lens housing 136. The adapter lens housing 136 includes means, such as engaging tabs 138, associated therewith for selectively attaching the adapter lens housing 134 to a housing associated with an ophthalmic lens system (not shown), such as the ophthalmic lenses shown in previous figures. The set 130 may also include another plus powered adapter lens 140 which may have a different nominal power than the adapter lens system 132. The set 130 may further include a minus power adapter lens system 145 having a predetermined minus power, and/or additional minus power adapter lens systems, such as lens system 150 which may have different nominal refractive powers. The set 130 may further include a contact lens adapter system 155, and additional contact lens systems such as a contact adapter lens 160, which may have different nominal refractive powers, and being plus and/or minus powered adapter lenses. The different adapter lenses act to modify the optical characteristics, such as the net power, magnification, or other characteristics of the ophthalmic lens system with which they are used in a selective and predetermined manner. The set 130 may further include one or more filter lenses 165 to also modify the optical characteristics of the ophthalmic lens system. It should be recognized that the set of adapter lenses 130 may vary to include plus or minus powered lenses, contact or non-contact lenses, each of which is designed to modify the optical characteristics of the ophthalmic lens system in a selective and predetermined manner.

As should be recognized from the foregoing, the adapter lenses of the invention may be used for modifying power and magnification of an ophthalmoscopic or gonioscopic lens system, or alternatively used to modify the imaging characteristics thereof. The adapter lenses may be designed to correct for imaging aberrations of the combined ophthalmoscopic lens system, and may use simple spherical or aspherical plano-convex, plano-concave, bi-convex, or bi-concave designs selectively positioned either in front of or behind the ophthalmoscopic lens system with which they are used. A wide variety of different power adapter lenses may be used in association with a particular ophthalmoscopic lens system to achieve various magnifications and system characteristics. The adapter lens systems may include one or more optical elements and may be of the non-contact or contact type. Additionally, various of the preferred embodiments as described herein may be combined and used in conjunction with one another and an ophthalmoscopic lens system to expand the application and use of the ophthalmoscopic lens system. Although preferred embodiments of the invention have been described, it is to be understood that various modifications would be obvious to those skilled in the art, and are embodied within the present invention as defined by the appendant claims.

What is claimed is:

1. An indirect ophthalmoscopy lens for use in the examination or treatment of a patient's eye, comprising, at least two lens elements, each having first and second co-axial surfaces with at least one of said lens elements including an aspheric surface of revolution with its magnitude and shape defined by the polynomial expressed as follows:

$$y=(2rx+(e^2-1)x^2)^{1/2}+Ax^F+Bx^G+Cx^H;$$

where r equals the apical radius of curvature of the surface, e equals apical eccentricity of the surface, and the coefficients A, B, and C equal successive terms in the polynomial, while F, G, and H equal exponents in the successive terms respectively, said at least two lens elements positioned adjacent one another at a distance less than the sum of the focal distances of said elements such that the refractive properties of each are combined, said at least two lens elements being positioned in spaced apart relationship to the patient's eye at a distance substantially corresponding to the focal length of the combination of said at least two lens elements, said at least two lens elements simultaneously collecting light rays emerging from points on the fundus of the patient's eye and refracting said emerging light rays to form an aerial image of the fundus.

2. The indirect ophthalmoscopy lens of claim 1, wherein, each of said at least two lens elements includes posterior and anterior surfaces relative to said patient's eye, with a first lens positioned nearest to said patient's eye and a second lens positioned further from said patients eye, wherein the anterior surface of said first lens and the posterior surface of said second lens are convex surfaces with at least one of said convex surfaces being an aspheric surface of revolution.

3. The indirect ophthalmoscopy lens of claim 2, wherein, said posterior surface of said first lens and the anterior surface of said second lens consist of a surface selected from the group of surfaces comprising a convex spherical surface, a convex aspherical surface, a plano surface and a concave surface.

4. The indirect ophthalmoscopy lens of claim 1, wherein, each of said at least two lens elements are biconvex lenses, with adjacent surfaces of each of said lens elements having a curvature which is more highly curved than the other surface of each said at least two lenses.

5. The indirect ophthalmoscopy lens system as recited in claim 1, wherein, one of said at least two lens elements is moveable relative to other of said lenses, with the position of said at least one lens being selectively variable to modify the optical characteristics of the combination of said at least two lenses.

6. The indirect ophthalmoscopy lens of claim 5, wherein, each of said at least two lenses include posterior and anterior surfaces respectively in relation to the patient's eye, wherein each of said posterior and anterior surfaces consist of a surface selected from the group of surfaces comprising a convex spherical surface, a convex aspherical surface, a plano surface and a concave surface.

7. The indirect ophthalmoscopy lens of claim 6, wherein, said at least one aspherical surface has continuous and progressive change in curvature peripheralward and is non-spherical over its extent.

8. The indirect ophthalmoscopy lens of claim 6, wherein, each of said at least two lens elements are biconvex lenses, with adjacent surfaces of each of said lens elements having a curvature which is more highly curved than the other surface of each of said at least two lenses.

9. The indirect ophthalmoscopy lens of claim 6, wherein, said optical characteristics of the combination of said at least two lenses comprise image magnification.

10. An adapter lens system for use with an ophthalmic lens system in the examination or treatment of a patient's eye comprising, at least one adapter lens element including first and second surfaces, said at least one adapter lens element being positioned within an adapter housing, said adapter housing being selectively attached to a housing associated with said ophthalmic lens system, said at least one adapter lens element being positioned in predetermined relation to a lens of said ophthalmic lens system, wherein said at least one adapter lens modifies the optical characteristics of said ophthalmic lens system in a selective and predetermined manner.

11. The adapter lens system of claim 10, wherein, said at least one adapter lens element is a plus powered lens which when selectively positioned relative to said ophthalmic lens system will increase the net power of said ophthalmic lens system.

12. The adapter lens system of claim 10, wherein, said at least one adapter lens element is a negative powered lens which when used in combination with said ophthalmic lens system will result in a predetermined net power for the combined optical system.

13. The adapter lens system of claim 10, wherein, said at least one adapter lens element is a non-contact lens.

14. The adapter lens system of claim 10, wherein, said at least one adapter lens element is a contact lens.

15. The adapter lens system of claim 10, wherein, said means for selectively attaching said adapter housing includes an outer surface on said adapter lens housing which is frictionally engageable on an interior surface of said housing of said ophthalmic lens system.

16. The adapter lens system of claim 15, wherein, said outer surface includes resilient means associated therewith for frictionally engaging said interior surface of said ophthalmic lens housing.

17. The adapter lens system of claim 16, wherein, said resilient means is an o-ring positioned on said outer surface which frictionally engages said interior surface and provides a seal between said adapter lens housing and said ophthalmic lens system housing.

18. The adapter lens system of claim 10, wherein, said at least one adapter lens element has at least one aspherical surface with its magnitude and shape defined by the polynomial expressed as follows:

$$y=(2rx+(e^2-1)x^2)^{1/2}+Ax^F+Bx^G+Cx^H;$$

where r equals the apical radius of curvature of the surface, e equals apical eccentricity of the surface, and the co-efficients A, B, and C equal successive terms in the polynomial, and F, G, and H equal exponents in the successive terms respectively, wherein at least the apical radius of curvature and apical eccentricity of said at least one aspheric surface are chosen to satisfy optical correction of image aberrations including curvature, astigmatism, and distortion.

19. The adapter lens system of claim 10, wherein, said at least one adapter lens element is selectively moveable along the optical axis of said ophthalmic lens system to modify the net power of the resulting optical system.

20. The adapter lens system of claim 10, wherein, said ophthalmic lens system is an indirect ophthalmoscopy lens system.

21. The adapter lens system of claim 10, wherein, said ophthalmic lens system includes a plurality of mirrors to view different portions of the fundus or anterior chamber angle, and said adapter lens system includes at least one lens element for each of said mirrors.

22. The adapter lens system of claim 10, wherein, said ophthalmic lens system is a direct ophthalmoscopy lens system.

23. A set of adapter lens systems for use with an ophthalmic lens system in the examination or treatment of a patient's eye, comprising:

at least two adapter lens systems, each having at least one adapter lens element positioned within an adapter lens housing, said adapter lens housing being selectively attachable to a housing associated with said ophthalmic lens system, wherein said at least two adapter lens systems are different from one another and modify the optical characteristics of said ophthalmic lens system in a selective and predetermined manner.

24. The set of adapter lens system's as in claim 23, wherein, said adapter lens systems include positive and negative power lens systems.

25. The set of adapter lens systems as in claim 23, wherein, said adapter lens systems include contact and non-contact lens systems.

26. An indirect ophthalmoscopy lens system comprising, at least two lenses positioned in spaced apart relationship along an optical axis such that the optical properties of said at least two lenses combine to form an aerial image of the fundus of a patient's eye, wherein at least one of said at least two lenses is moveable relative to the other of said lenses, with the position of said at least one lens being selectively variable to modify the optical characteristics of the combination of said at least two lenses.

27. The indirect ophthalmoscopy lens system as recited in claim 26, wherein, at least one of said two lenses includes at least one surface being an aspheric surface of revolution.

28. The indirect ophthalmoscopy lens system of claim 26, wherein, one of said at least two lenses is a plus powered lens and the other is a negative powered lens, wherein said negative powered lens provides increased magnification when moved relatively toward or positioned immediately adjacent to said plus powered lens.

29. The indirect ophthalmoscopy lens system of claim 26, wherein, said at least two lenses are plus powered lenses, wherein said plus powered lenses provide decreased magnification when one of said plus powered lenses is moved relatively toward or positioned immediately adjacent to the other of said plus powered lenses, and said plus powered lenses provide increased magnification when one of said plus powered lenses is moved relatively away from the other of said plus powered lenses.

30. The indirect ophthalmoscopy lens of claim 26, wherein, said at least one lens is moveable to modify the net power of the combination of said at least two lenses forming the indirect ophthalmoscopy lens system.

31. The indirect ophthalmoscopy lens of claim 26, further comprising, a contact lens positioned in space relationship to said at least two lenses, said contact lens including a posterior surface for placement upon the cornea of said patient's eye.

* * * * *